United States Patent [19]

Ishibashi et al.

[11] 4,014,652

[45] Mar. 29, 1977

[54] AUTOMATIC ANALYTIC APPARATUS OF LIQUIDS

[75] Inventors: Wataru Ishibashi, Kunitachi; Shigenobu Taira; Ken Migita, both of Kawasaki, all of Japan

[73] Assignee: Showa Denko Kabushiki Kaisha, Tokyo, Japan

[22] Filed: Sept. 18, 1975

[21] Appl. No.: 614,763

[30] Foreign Application Priority Data

Sept. 27, 1974 Japan .......................... 49-111055
Dec. 26, 1974 Japan .......................... 50-148373
Dec. 27, 1974 Japan .................................. 50-532

[52] U.S. Cl. ............................... 23/253 R; 356/36
[51] Int. Cl.² .................... G01N 1/10; G01N 33/00
[58] Field of Search ........... 23/253 R, 259; 356/36, 356/181

[56] References Cited

UNITED STATES PATENTS

| 2,899,280 | 8/1959 | Whitehead et al. ......... 23/253 R X |
| 3,442,623 | 5/1969 | Aegidius ........................ 356/184 X |
| 3,505,021 | 4/1970 | Eveleigh ......................... 23/230 R |

*Primary Examiner*—Robert M. Reese
*Attorney, Agent, or Firm*—Carroll F. Palmer

[57] ABSTRACT

An automatic analytic apparatus of liquids has a liquid analyzer; a gas-admissible tube connected to the analyzer so as to conduct a liquid thereto; and means to collect a specified amount of liquid sample being analyzed, and, each time the collected amount of said liquid reaches said specified amount, automatically carry the liquid sample batch forward with a prescribed amount of air or any other inert gas interposed between the adjacent batches of said liquid sample, thus continuously passing alternate series of flowing liquid and gas batches respectively having a predetermined quantity through the above-mentioned tube.

10 Claims, 9 Drawing Figures

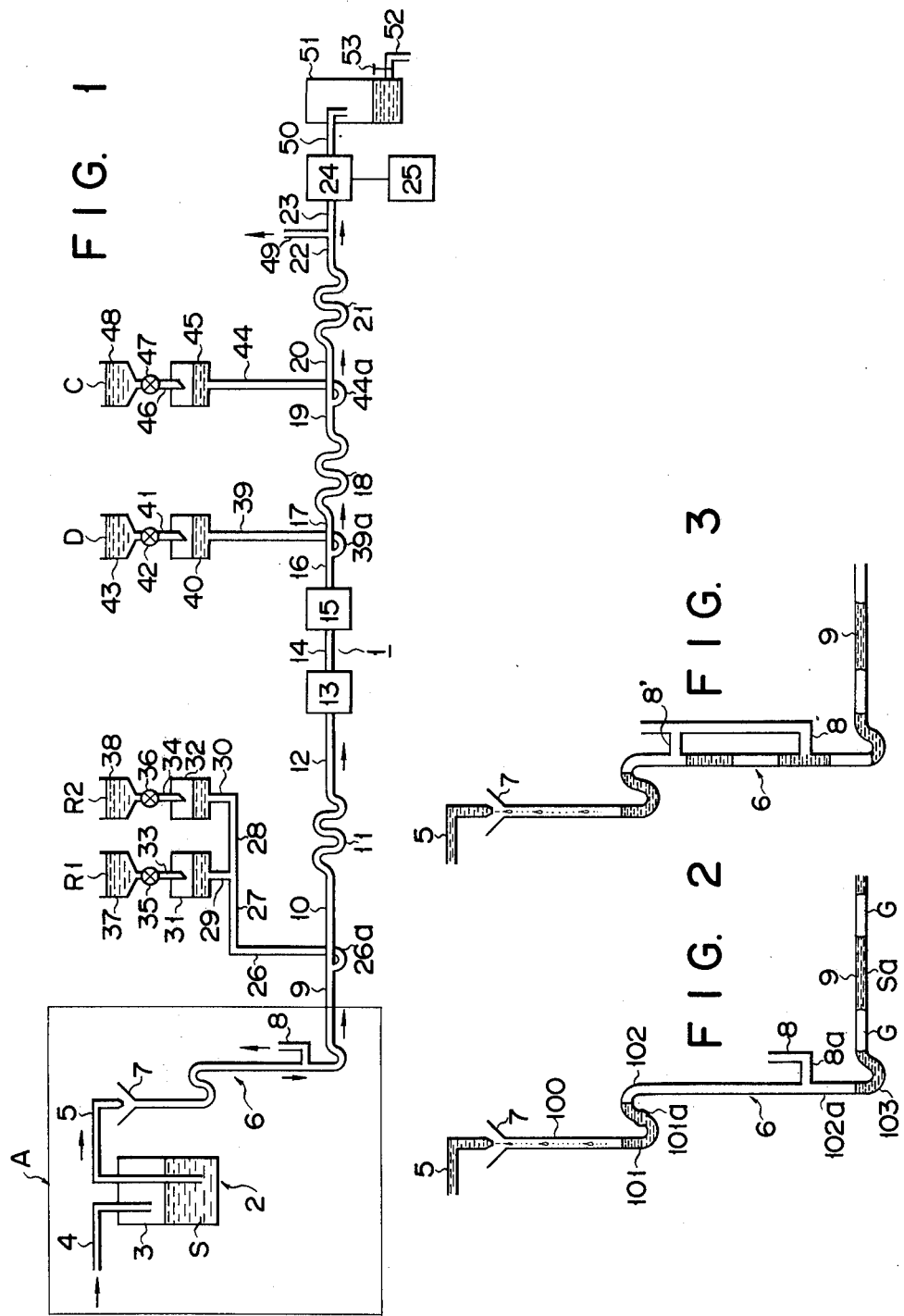

AUTOMATIC ANALYTIC APPARATUS OF LIQUIDS

BACKGROUND OF THE INVENTION

I. Field of the Invention

This invention relates to an apparatus for automatically and continuously analyzing a liquid sample and more particularly to a liquid-analyzing apparatus equipped with a device designed continuously to pass a liquid sample through a tube included in the apparatus characteristically in the form divided into batches each having a prescribed quantity by interposing a preset amount of gas between the adjacent batches of said liquid sample.

II. Description of Prior Art

Generally, devices for automatic chemical analysis of a liquid sample are broadly classified into the discrete and continuous flow types. The discrete type required a considerable amount of a liquid sample and liquid reagent to be used for each analytic operation, through it did not pose any problem in respect to construction. Further, the discrete type analytic apparatus had the drawbacks that upon completion of each analysis, the interior contamination of said apparatus caused by the preceding sample had to be cleaned off, before the succeeding one was analyzed; said cleaning was a troublesome work consuming much the same length of time as analysis itself; where numerous kinds of sample were analyzed by the above-mentioned discrete type apparatus, the analytic work even required a longer time than when as many kinds of sample were manually analyzed; and elimination of the interior contamination of the apparatus was not actually carried out so satisfactorily as it should be, resulting in a gradual decline in the precision of analysis, where the apparatus was used at a close interval.

A continuous flow type analytic apparatus improved on the above-mentioned discrete type is set forth, for example, in the U.S. Pat. No. 2,899,280. With said United States patent, an elastic tube is squeezed, for example, by a proportioning pump, giving rise to the continuous flow of a sample or any other liquid. Air introduced by the proportioning pump through another elastic tube branching from the first mentioned elastic tube is forcefully carried into the liquid running through the first mentioned tube. Thus alternate series of batches of liquid sample and the air respectively having a prescribed quantity run through that portion of a main tube which follows the converging point of both liquid and air tubes. The batches of the liquid sample are successively analyzed by an analyzer positioned ahead of the mixed streams of liquid and air. As the mixed streams flow onward through the main tube, the batches of air included in the mixed streams cleans off the internal contamination of the main tube caused by the preceding batches of liquid sample. With such an apparatus as disclosed in said United States Patent, the cleaning effect of the air batches enables analysis to be carried out with few errors even when said apparatus is repeatedly operated to analyze on kind of sample after another at a close interval. Though it indeed has a prominent power of analyzing numerous kinds of sample with high precision, yet the analytic apparatus such as disclosed in the above-mentioned United States Patent still has the drawbacks that the flow rates of a liquid sample and air which jointly act to define the quantity of the batches of the liquid should be very closely controlled and also are limited by the pressure applied by a pump and the inner diameter of the elastic tubes of the liquid and air; the elastic tubes of the liquid and air which are frequently squeezed by the pump are subject to wear and eventually to breakage during a long period of use; and, when the inner walls of said tubes are exposed to organic solvents, strong acids or strong alkalis, particularly at a high temperature, the tubes as a whole are corroded or become brittle to remain resilient, resulting in the failure to maintain the quantities of the batches of the liquid and air at prescribed levels.

SUMMARY OF THE INVENTION

It is accordingly an object of this invention to provide an automatic analytic apparatus of liquids which is concurrently possessed of the durability of the discrete type analytic apparatus and the prominent power of analysis and contamination cleaning displayed by the continuous flow type analytic apparatus.

Another object of the invention is to provide an automatic analytic apparatus of liquids which is equipped with a device for preparing batches from a liquid sample, each said batch having a prescribed quantity, by interposing batches of gas between the adjacent liquid batches, before a reagent, for example, is added to the liquid sample, thereby forming alternate series of batches of flowing liquid and air.

Another object of the invention is to provide an automatic analytic apparatus of liquids which produces the alternate series of batches of flowing liquid and air by means of a gravitational force, without forcefully producing said mixed streams by means of a pump.

Still another object of the invention is to provide an automatic analytic apparatus which generates the above-mentioned alternate series of batches of flowing liquid and air on the basis of interrelationship between the inner diameter of a tube used on one hand and an interfacial tension occurring between the liquid and air on the other.

A further object of the invention is to provide an automatic analytic apparatus which, even after being used for a long period, enables the alternate series of batches of liquid and air to flow through a main tube without any change in the quantities specified for both elements.

A still further object of the invention is to provide an automatic analytic apparatus of simple arrangement which can easily produce the alternate series of batches of flowing liquid and air respectively having a preset quantity.

These and other objects which will be apparent from the following detailed description are attained by an automatic analytic apparatus of liquids which comprises an analyzer for analyzing a liquid sample qualitatively or quantitatively, said analyzer being provided with an inlet and outlet for the liquid sample; tubular guiding means, one end of which is connected to the inlet of the analyzer so as to conduct the liquid sample thereto for analysis; and a batch flowgenerating means to collect a prescribed amount of liquid sample being analyzed, and each time the collected amount thereof reaches said preselected level, automatically carry the liquid sample batch forward with a specified amount of gas interposed between the adjacent batches of said liquid sample, thus continuously passing alternate series of flowing liquid and gas batches respectively having a predetermined quantity through said tubular guiding means, and wherein said tubular quiding means has a small inner diameter sufficient to maintain an interface between the respective adjacent batches of flowing liquid and gas.

With the above-mentioned device included in the analytic apparatus of this invention which is designed to generate alternate series of batches of flowing liquid and gas, the liquid is carried forward, each time it is collected to a specified amount, by the principle of a siphon as later described, according to interrelationship between the inner diameter of the tubular guiding means on one band and an interfacial tension between the liquid and gas on the other or by the force of compressed or sucked gas stream. Namely, a necessarily defined amount of gas is interposed between the respective adjacent batches of liquid. The appended drawings show the various concrete arrangements of the aforesaid device for producing the alternate series of batches of flowing liquid and gas. The analytic apparatus of this invention can be applied in broad fields such as various chemical analyses, medical clinical examinations and analyses of the effects of environmental pollution.

BRIEF DESCRIPTION OF THE DRAWING

This invention will be more fully understood from the following detailed description when taken in conjunction with the accompanying drawings in which:

FIG. 1 is a schematic side view of an analytic apparatus embodying this invention;

FIG. 2 is a schematic enlarged side view of a batch flow-generating device included in the analytic apparatus shown in FIG. 1;

FIG. 3 is a schematic side view of a modification of the batch flow-generating device of FIG. 2;

DETAILED DESCRIPTION OF THE PREFERRED EMBODIMENTS

Figure 4:
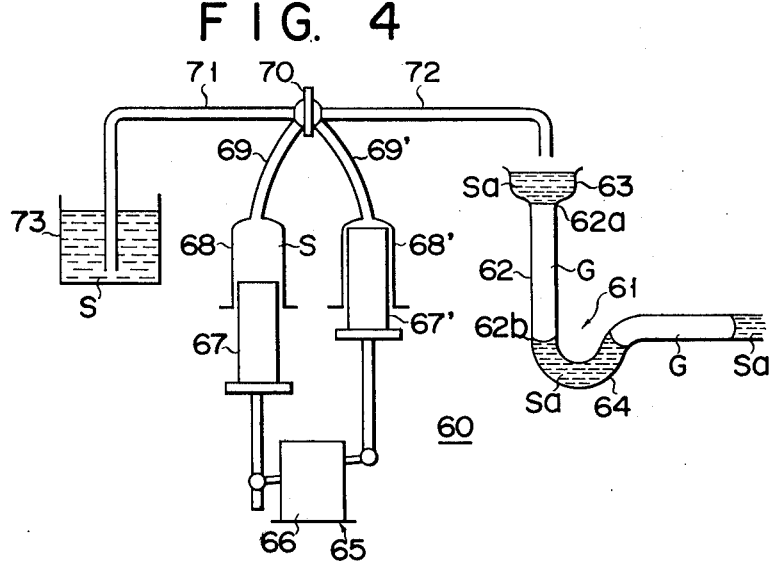
FIG. 4 is a schematic side view of another embodiment of the batch flow-generating device used with the analytic apparatus of the invention.

FIG. 1 shows an analytic apparatus according to this invention provided with a batch flow-generating device utilizing the principle of a siphon. This analytic apparatus 1 is equipped with a batch flow-generating device A for producing alternate series of batches of flowing liquid and gas which comprises a liquid sample supplier 2 constituted by a sealed liquid sample container 3 which is provided with a tube 4 for air or any other inert gas and a liquid sample or connection tube 5, and the later described liquid and gas batch generator 6. Referring to the liquid sample supplier 2, one inner end of the gas tube 4 is inserted into the free space of the liquid sample container 3 and positioned above the surface of the liquid sample S. A gas carried into the liquid sample container 3 through the other outer end of the gas tube 4 by a pump or any other means presses the surface of the liquid sample S. The gas pressure causes the liquid sample S to be conducted to the liquid and gas batch generator 6 through the connection tube 5. One end of the connection tube 5 extends far below the surface of the liquid sample S down to a print close to the bottom of the liquid sample container 3, and the other end of said connection tube 5 is open to the atmosphere surrounding the entire analytic apparatus. The liquid sample S is brought into the liquid and gas batch generator 6 at a prescribed rate. Said other end of the connection tube 5 is preferred to have a smaller diameter than the inner diameter of the main tube of the analytic apparatus 1.

The sample liquid S brought through the connection tube 5 passes through the liquid and gas batch generator 6 provided with a funnel-shaped mouth 7 and a branch tube 8 for eliminating an excess amount of gas. During the above-mentioned passage, the liquid sample forms a series of batches separated from each other by a prescribed amount of intervening gas. The liquid and gas batch generator 6 will be later described more in detail. Alternate series of batches of flowing liquid and gas thus formed pass through a horizontal tube 9 connected to the outlet of the liquid and gas batch generator 6. For example, reagents $R_1$ and $R_2$ are supplied to each of the liquid batches through a vertical pipe 26 connected to the outlet of said horizontal tube 9. A liquid batch consisting of the batch of the liquid sample S and reagents $R_1$ and $R_2$ travels together with a gas batch through a horizontal tube 10 connected to the first mentioned horizontal tube 9 and then to a mixing tube 11. This mixing tube 11 is formed of a tube extending in zigzags in the same plane, thereby causing the liquid sample S and reagents $R_1$ and $R_2$ to be fully mixed during transit therethrough, because the upper and lower end portions of said liquid batch are reversed in succession. The mixed liquid batch passes through a horizontal tube 12 connected to the mixing tube 11 and then to a heater 13, where the liquid batch is heated for full reaction between the liquid sample S and reagents $R_1$ and $R_2$. The mixed liquid batch which has left the heater 13 after completion of said reaction is carried through a horizontal tube 14 connected to the heater 13 and then to a cooler 15 to be cooled therein.

The mixed liquid batch which has been drawn out of the cooler 15 after fully cooled is conducted to a horizontal tube 16 connected to the cooler 15. In said horizontal tube 16, for example, a diluent D is added to the mixed liquid batch through a vertical tube 39 of the same type as the aforesaid vertical tube 26. The liquid batch now containing the diluent D is transferred to a horizontal tube 17 connected to the preceding horizontal tube 16 and then to a mixing tube 18 of the same type as the mixing tube 11, where the components of the mixed liquid batch are more fully mixed. Upon completion of said mixing, the mixing liquid batch is sent to a horizontal tube 19 connected to the outlet of the mixing tube 18. At this point, a color reagent C is added to the mixed liquid batch through a vertical tube 44 of the same type as the first mentioned vertical tube 26. The mixed liquid batch now containing the color reagent C moves through a horizontal tube 20 and ten to a mixing tube 21 of the same type as the previously mentioned mixing tube 11.

The color reagent C is fully mixed with the liquid sample batch S in the mixing tube 21. The mixed liquid batch delivered from the mixing tube 21 is brought into a horizontal tube 22 connected to the mixing tube 21.

A gas batch intervening between the respective adjacent batches is removed through an exhaust tube 49 rising upward from the outlet of the horizontal tube 22. The liquid batch separated from the gas batch passes through a horizontal tube 23 connected to the preceding horizontal tube 22 and then to a qualitative or quantitative analyzer, such as a colorimeter 24 to be subjected to the required analysis. The liquid batch whose analysis has been completed is discharged through a horizontal tube 50 connected to the outlet of the colorimeter 24.

The results of analysis by the colorimeter 24 recorded by a recorder 25 interlockingly operated with the colorimeter 24. The colorimeter and recorder used with the analytic apparatus of this invention may consist of any known type, description thereof being omitted.

As best shown in FIG. 2, the liquid and gas batch generator 6 is provided with a vertical tube 100 whose mouth 7 has a funnel shape. The lower end of the vertical tube 100 is connected to a U-shaped tube 101 which receives a specified amount of liquid sample and performs a siphoning action. A vertical tube 102 is connected to the outlet of said siphoning tube 101 with the connection of said vertical tube 102 and the siphoning tube 101 made smooth to effect easy siphoning. A U-shaped tube 103 is provided as a liquid sample receptacle at the lower end of the vertical tube 102. The U-shaped liquid sample receptacle 103 is preferred to have the same capacity as the U-shaped siphoning tube 101. A branch tube 8 is communicatively attached to the side wall of the vertical tube 102 and opened to the atmosphere surrounding the batch flow-generating device A. An amount of gas held in that portion 102a of the vertical tube 102 which is defined between the junction of the branch tube 8 and said vertical tube 102 and the junction of said vertical tube 102 and liquid sample receptacle tube 103 is successively brought into the horizontal tube 9 in the form of a gas batch G separating the respective adjacent liquid batches Sa.

A liquid sample S supplied through the connection tube 5 so as not to close up the vertical tube 100 is collected in the U-shaped tube 101. Said supply of liquid sample may be effected by dropping the liquid sample from the tip end of the connection tube 5 or by conducting the liquid sample along the inner wall of the vertical tube 100 into the siphoning tube 101. Where any slight additional amount of liquid sample S is brought to the liquid sample batch Sa which has already filled the U-shaped tube 101 in an equilibrium state as shown in FIG. 2, then said equilibrium is broken, causing the liquid sample batch Sa previously filled in the U-shaped tube 101 to fall down through the vertical tube 102. The liquid sample S falling down through the vertical tube 102 applies pressure on the gas held in said vertical tube 102, causing the gas to be expelled into the atmosphere through the branch exhaust tube 8. A gas held in the tube 102a, that is, between the lower end 8a of the branch exhaust tube 8 and that level of the liquid sample batch Sa collected in the U-shaped receptacle tube 103 by the initial operation of the batch flow-generating device A which faces the inlet side of said receptacle tube 103 fails to escape, and cooperates with the falling liquid sample S to push the liquid sample batch Sa already collected in the receptacle tube 103 into the horizontal tube 9. Now, the falling liquid sample S is collected in said receptacle tube 103 in place of the preceding liquid sample batch Sa. Thus, liquid sample batches Sa respectively having a prescribed quantity and separated from each other by the intervening gas batches G having a specified amount are produced in succession to be carried into the following sections of the subject analytic apparatus in turn.

However, it sometimes happens that a portion of the succeeding liquid sample batch Sa is untimely brought into the U-shaped tube 101 under the condition where the preceding sample batch Sa already collected in said U-shaped tube 101 has just begun to fall down through the vertical tube 102, and the rear end portion of said liquid sample batch Sa is still positioned near the outlet of the U-shaped tube 101, namely, before said collected liquid sample batch Sa passes the exhaust branch tube 8. In such case, the incoming portion of the succeeding liquid sample batch Sa is also drawn into the vertical tube 102 together with the preceding liquid sample batch Sa, which has now begun to fall down through said tube 102, with the result that the preceding liquid sample batch having a larger amount than prescribed is carried into the horizontal tube 9. To avoid such undesirable event, the intermediate part 101a of the outlet section of the U-shaped tube 101 is made to have a larger inner diameter than that of the main tube. As the result, a portion of the succeeding liquid sample batch Sa which is untimely brought into the U-shaped tube 101 before the preceding liquid sample batch Sa fully leaves said tube 101 is stopped in said swelled out of bulged intermediate part 101a and does not go beyond, thereby being prevented from running together with the preceding liquid sample batch Sa. Therefore, the remaining portion of the succeeding liquid sample batch Sa which is carried into the U-shaped tube 101 through the connection tube 5 and vertical tube 100 directly converges with the aforesaid one portion which is already stopped in he swelled out intermediate part 101a of the U-shaped tube 101, thereby preventing the said one portion of the succeeding liquid sample batch Sa from falling down through the vertical tube 102 in the state where any gas is interposed between said one portion of the succeeding liquid sample batch and preceding liquid sample batch Sa.

As apparent from the foregoing description, the flowing speed of the liquid sample batch Sa is governed by the time required for the U-shaped siphoning tube 101 to be fully filled with liquid sample brought thereinto through the connection tube 5 and vertical tube 100. Said time can be adjusted by the inner diameter of the connection tube 5 and the pressure of a compressed gas passing through the gas tube 4. Where said time is short, that is, where liquid sample batches are supplied one after another in rapid succession to the batch flow generator A, then that opening of the exhaust branch tube 8 which faces the vertical tube 102 tends to be closed up by any of the rapidly introduced liquid sample batches. Under such condition, a given liquid sample batch Sa fully filled in the U-shaped siphoning tube 101 can not fall down through the vertical tube 102 even when the normal equilibrium state of said liquid sample batch Sa is broken. As the result, the amount of the liquid sample batch Sa collected in the U-shaped tube 101 exceeds a prescribed level, until the above-mentioned opening of the branch exhaust tube 8 is released by any other falling liquid sample batch for communication with the open air, thus making it substantially impossible to conduct liquid sample batches successively through the main tube in the prescribed amount. To avoid such difficulties, it is advised to provide another exhaust branch tube 8' above the first mentioned exhaust branch tube 8 separately therefrom or in connection therewith as shown in FIG. 3. This arrangement causes the vertical tube 102 to be communicated with the open air through the upper exhaust tube 8' even when the lower exhaust tube 8 has its opening closed up, as shown in FIG. 3, by any falling liquid sample batch S$a$, thereby enabling a series of liquid sample batches each having a prescribed quantity to be produced without any obstruction.

Reverting to FIG. 1, reagents, diluents and color reagents are added to the liquid sample batches running through the various sections of the horizontal main tube through the vertical tubes 26, 39, 44 corresponding to said sections. U-shaped tubes 26$a$, 39$a$, 44$a$ are connected to the lower end of the vertical tubes 26, 39, 44 respectively. The above-mentioned additives run upward through the U-shaped tubes 26$a$, 39$a$, 44$a$ from the underside of the corresponding sections of the horizontal main tube to be supplied to the liquid sample batches. The amounts of the additives supplied to the liquid sample batches are determined by the pressure applied by said additives and the inner diameter of the vertical tubes 26, 29, 30, 39, 44. The pressures exerted by the additives are adjusted by a height from the level of said additives held in the storage tanks 31, 32, 40, 45 to the general height of the main tube, and external pressure applied to the surface of the additives received in the containers thereof 37, 38, 43, 48. The levels of the additives in the storage tanks 31, 32, 40, 45 which decrease by discharging the prescribed amounts of said additives are restored by fresh amounts thereof brought into the storage tanks 31, 32, 40, 45 from the containers 37, 38, 43, 48 through the corresponding supply tubes 33, 34, 41, 46 by the operation of the corresponding valves 35, 36, 42, 47. FIG. 1 represents the embodiment wherein two reagents $R_1$ and $R_2$ are added to the liquid sample batches at the same time. A vertical tube 30 connected to the bottom of the storage tank 32 communicates with a vertical tube 29 connected to the bottom of the storage tank 31 through a horizontal connection tube 28. The two reagents $R_1$ and $R_2$ which converge with each other at the junction of the vertical tube 29 and the horizontal connection tube 28 are conducted through a horizontal tube 27 to the vertical tube 26.

The final outlet of the analytical apparatus may be left open. Or it is possible, as shown in FIG. 1, to insert a tube 50 into a vessel 51 with the outlet of said tube 50 positioned above the level of a liquid held in said vessel 51, discharge said liquid through an outlet tube 52 by controlled operation of a cock 53 in a larger amount tha the unit time flow rate of consecutive liquid sample now separated from gas, and draw off said liquid sample through the tube 50 by the resultant suction force, thereby causing the liquid sample batches to travel through the horizontal main tube at a fixed speed.

The inner diameter of the horizontal main tube through which liquid sample batches are carried in a state separated from each other by intervening gas batches is chosen, as naturally expected, to have a sufficient small inner diameter to prevent a liquid-gas interface from being destroyed. This is, the inner diameter should be small enough to maintain an interface between the respective adjacent batches of liquid and gas. The inner diameter varies with an interfacial tension between the gas and liquid used.

There will now be described the case where the analytic apparatus of this invention shown in FIG. 1 is applied to the quantitative analysis of water-soluble phosphate included, for example, in a high compound fertilizer. A liquid sample of high compound fertilizer is taken into the container 3. Air is brought thereinto under pressure through the tube 4 by a pump (not shown), causing the liquid sample S to fall down through the connection tube 5. The liquid sample passes through the liquid and gas batch generator 6 to be formed into liquid batches separated from each other by intervening air batches. In this case, the liquid batch is chosen to travel through the horizontal main tube at a flow rate of, for example, 0.16 ml/min. The U-shaped tube 103 is accordingly specified to have a capacity of, for example, 3.9 ml/min. The liquid sample batches S$a$ run through the horizontal tube 9 in a state separated from each other by intervening air batches G. A (1 : 1) aqueous solution of nitric acid ($R_1$) and a color adjusting agent ($R_2$) consisting of a 2% aqueous solution of citric acid are added to the liquid sample batch S$a$ through the U-shaped tube 26$a$. The flow rates of the aqueous solutions of nitric acid and citric acid are set at 0.32 ml/min and 0.80 ml/min respectively. In this case, the air batch G is free from any of said additives, because the pressure of said air batch G prevents the additives from being carried thereinto. The mixed liquid batch is fully mixed in the zigzag-shaped mixing tube 11, while the mixed liquid sample batch travels through that portion of the horizontal main tube which is inserted into the heater 13 such as an oil bath maintained at a temperature of, for example, 95° C, reaction takes place between the phosphate and nitric acid included in said mixed liquid sample batch, causing all the phosphate contained therein to be converted into the ortho type. The mixed liquid sample batch is cooled by the cooler 15. Water is added as a diluent to the mixed liquid sample batch through the U-shaped tube 39$a$. The flow rate of the water is set, for example, at 3.9 ml/min. The liquid batch now containing water is subjected to thorough mixing in the zigzag-shaped mixing tube 18. Thereafter, a mixed color reagent solution [$NH_4VO_3.(NH_4)_6Mo_7O_{27}.HNO_3$] is supplied to the liquid sample batch now containing water at a rate of, for example, 1.2 ml/min through the U-shaped tube 44$a$.

After the liquid sample batch containing the color reagent is subjected to full mixing in the zigzag-shaped mixing tube 21, air batches G interposed between the adjacent liquid sample batches are expelled through the branch tube 49. The liquid sample batches now freed of air collectively take an integral from ready for analysis. The integral mass of the liquid sample flows through a horizontal tube 23 to a colorimeter 24 to be analyzed thereby. The results of analysis are recorded in a recording section connected to the colorimeter 24. The liquid sample whose analysis has been completed is discharged through the terminal tube 50.

Depending on the kind of a liquid sample being analyzed, it is unnecessary to provide the preceding sections of the analytic apparatus which are related to the addition of reagents $R_1$, $R_2$ and diluent D, but only the section associated with the addition of the color reagent C is required. In such case, the arrangements for $R_1$, $R_2$ and D, heater 13 and cooler 14 may be omitted. Further, the analyzer may consist, in addition to the aforesaid colorimeter, of a specific ion electrode meter, atomic absorption spectrophotometer, flame photoelectric photometer of fluorescence photoelectric photometer. Where any of the above-mentioned additional types of analyzer is applied, the kind of reagent being added to a liquid sample and the mechanism for effecting said addition will be obvious to those skilled in the art.

FIG. 4 present another form of batch flow-generating device 60 used with the analytic apparatus of this invention. This batch flow-generating device 60 comprises a liquid and gas batch generator 61 and a liquid supplier 65 for conducting a liquid to said liquid and gas batch generator 61. The liquid and gas batch generator 61 is formed of a vertical tube 62 provided with an inlet 62a and outlet 62b for the liquid sample, a liquid sample receptacle 63 connected to the inlet 62a and U-shaped tube 64 acting as a liquid sample receiver, one end of said U-shaped tube 64 being connected to the outlet 62b, and the other end thereof being connected to the horizontal tube 9 of FIG. 1.

The inner diameter of the vertical tube 62 is chosen to be sufficiently small to prevent a liquid-gas interface from being destroyed. Said inner diameter varies with an interfacial tension between the gas and liquid sample used. The liquid sample supplier 65 intermittently sends forth a prescribed amount of liquid sample to the liquid and gas batch generator 61. the supplier 65 may consist of any type, provided it can intermittently deliver a specified quantity of liquid sample substantially at one time. A liquid sample supplier illustrated in FIG. 4 is provided with drive means 66 for moving pistons 67, 67' alternately at a specified time interval. The pistons 67, 67' alternately moved vertically by the drive means 66 cause a liquid sample S held in a storage tank 73 to be sucked into one of cylinders 68, 68' through a horizontal tube 71 and also a liquid sample S brought into the other of said cylinders 68, 68' to be carried to the liquid and gas batch generator 61 through another horizontal tube 72. The above-mentioned alternate operation is effected by a valve mechanism 70. For example, where the piston 67 is brought down and the piston 67' is lifted, then the tubes 71 and 69 communicate with each other to carry the liquid sample S into the cylinder 68, and the tubes 72 and 69' communicates with each other to supply the liquid sample S to the liquid and gas batch generator 61. Such valve mechanism 70 is well known to those skilled in the art, detailed description thereof being omitted.

The amount of liquid sample S delivered to the liquid and gas batch generator 61 is fixed by defining the stop position of the pistons 67, 67' in the corresponding cylinders 68, 68'. However, the amount supplied should be sufficiently larger to overcome a liquid-gas interfacial tension occurring at the inlet of the vertical tube 62 of the liquid and gas batch generator 61 (said interfacial tension is hereinafter taken to mean an interfacial tension between the liquid sample brought into the liquid and gas batch generator 61 and the gas held in the vertical tube 62).

The liquid sample S sent forth from the supplier 65 is kept in the liquid sample batch receptacle 63 by the liquid-gas interfacial tension, while the amount of the liquid sample S is not collected in the receptacle 63 in a sufficiently large amount to destroy said interfacial tension. When the fully collected amount of the liquid sample batch Sa overcomes the liquid-gas interfacial tension, the entire liquid sample batch Sa falls down through the vertical tube 62 in a state fully filling the crosswise space thereof to be collected in the U-shaped liquid sample batch receiver tube 64. Air is already present in the vertical tube 62, before the succeeding liquid sample batch Sa collected in the liquid sample batch receptacle 63 falls down through the vertical tube 62 in the aforementioned manner. The air occupies the internal space of the vertical tube 62 defined between the inlet thereof and the level of the preceding liquid sample batch Sa already received in the U-shaped liquid sample batch holder tube 64. The air occupying said space is pressed downward by the succeeding liquid batch Sa which has been discharged from the liquid sample batch receptacle 63 and runs down the vertical tube 62 together with said succeeding liquid sample batch Sa. The above-mentioned process causes a series of liquid sample batches Sa respectively having a predetermined quantity and separated form each other by intervening air batches G respectively having a specified quantity, namely, alternate series Sa/G of both batches to be successively carried into the analytic apparatus. The amount of each air batch G is defined by a space lying between the inlet of the vertical tube 62 and that level of the liquid sample batch Sa received in the U-shaped holder tube 64 which faces said vertical tube 62.

Figure 5:
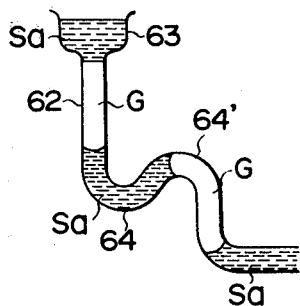
FIG. 5 is a schematic side view of a modification of the batch flow-generating device of FIG. 4.

It is possible to provide, as shown in FIG. 5, a curved vertical tube 64' connected to the outlet of the U-shaped liquid sample batch holder tube 64 so as to give rise to a siphoning action therebetween. This arrangement attains the easy flow of the liquid sample batch Sa.

Figure 6A:
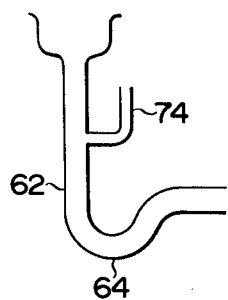
FIGS. 6A and 6B are schematic side views of other modifications of the batch flow-generating device of FIG. 4.
Figure 6B:
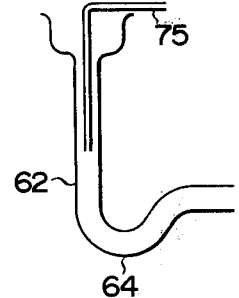

Further, the vertical tube 62 may be provided, as shown in FIGS. 6A and 6B, with an exhaust tube communicating with the open air. For example, a branch exhaust tube 74 similar to the aformentioned branch tube 8 may be fitted, as shown in FIGS. 6A, to the vertical tube 62 to establish communication between said vertical tube 62 and the open air. Or a separate communication tube 75 may be inserted into the vertical tube 62 through the liquid sample batch receptacle 63 to attain communication between said vertical tube 62 and the open air. In these cases, the quantity of the air batch is defined by that internal space of the vertical tube 62 which extends from the lower end of the exhaust tube 74 of 75 to that upper end of the U-shaped liquid sample batch holder tube 64 which faces the vertical tube 62. Provision of the above-mentioned exhaust tube 74 or 75 offers a larger latitude in specifying the quantity of the air batch G.

Figure 7:
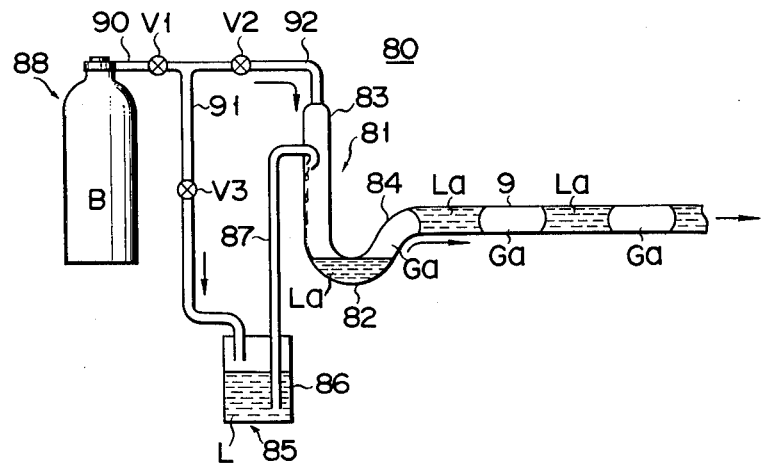
FIG. 7 is a schematic side view of still another embodiment of the batch flow-generating device used with the analytic apparatus of the invention.

FIG. 7 sets forth another embodiment of the batch flow-generating device 80 which is well adapted for use with the analytic apparatus of this invention. This batch flow-generating device 80 comprises a liquid and gas batch generator 81, a liquid sample batch supplier 85 for conducting a liquid sample to the liquid and gas batch generator 81 at a specified flow rate, and a gas supplier 88 for delivering gas to the liquid and gas batch generator 81 at a prescribed flow rate. The liquid and gas batch generator 81 is formed of the later described curved liquid sample batch receptacle tube 82 for collecting a predetermined quantity of liquid sample, and an inlet tube 83 and outlet tube 84 both for said receptacle 82. The outlet tube 84 is connected to the horizontal tube 9 of FIG. 1.

The liquid sample L is continuously supplied from the supplier 85 to the tubular liquid sample batch receptacle 82 at a prescribed flow rate so as not to fill up the inlet tube 83. A gas is conducted from the air supplier 88 to the inlet tube 83 at a specified flow rate. The liquid and gas suppliers 85, 88 may be of any type. With the embodiment of FIG. 7, both suppliers are coupled to each other. A compressed gas holder, for example, a compressed nitrogen gas cylinder B sends forth a portion of compressed nitrogen gas to a liquid sample storage tank 86 containing a liquid sample L. During transit, said portion of the compressed nitrogen gas has its pressure decreased by a pressure-reducing valve $V_1$. The nitrogen gas passes through a branch tube 91 diverted from a gas tube 90 to have its flow rate controlled to a prescribed level by a flow rate control valve $V_3$ and is brought into the storage tank 86 containing the liquid sample L to apply pressure on the surface of the liquid sample L. The liquid sample storage tank 86 is provided with a vertical liquid sample tube 87, one end of which is inserted into the liquid sample L and the other end of which opens to the interior of the inlet tube 83. The liquid sample L pressurized by the compressed nitrogen gas flows upward through the vertical supply tube 87 into the liquid sample batch receptacle 82. On the other hand, the remaining portion of the compressed nitrogen gas runs through a flow rate control valve $V_2$ into the inlet 83 at a present flow rate through a tube 92. Obviously, this tube 92 is hermetically connected to the inlet tube 83.

The liquid sample L and compressed nitrogen gas are present together in the inlet tube 83 of the liquid and gas batch generator 81. Namely, the liquid sample L is carried to the liquid sample batch receptacle 82 from the supplier 85 so as not to fill up the inlet tube 83. This flow of the liquid sample L is attained by disposing the liquid sample outlet of the vertical supply tube 87 close to the inner wall of the inlet tube 83, for example, so as to cause the liquid sample L to run along the inner wall of the inlet tube 83.

Where the liquid sample L delivered from the supplier 85 at a predetermined flow rate is collected in the tubular liquid sample batch receptacle 82 in a predetermined amount to shut off the passage of nitrogen gas stream therethrough, namely, where the level of the liquid sample L reaches the root portion of the upper wall of the U-shaped liquid and gas batch generator 81 (the condition indicated in FIG. 7), then the entire liquid sample batch L now having a prescribed quantity is pushed toward the outlet tube 84 by the compressed nitrogen gas continuously sent forth from the nitrogen gas supplier 88 to form one liquid sample batch La. The compressed nitrogen gas continues to push the liquid sample batch La until the succeeding portion of the liquid sample L is fully collected in the now vacant space of said receptacle 82. At this point, the compressed nitrogen gas pushes the succeeding liquid sample batch, forming a nitrogen gas batch Ga which occupies a space extending from the level of the succeeding liquid sample batch La which touches the aforesaid root portion of the upper wall of the U-shaped liquid and gas batch generator 81 and the rear end face of the preceding liquid sample batch La. Thus, a series of liquid sample batches La respectively having a prescribed quantity separated from each other by intervening nitrogen gas batches Ga respectively having a specified quantity, namely, alternate series La/Ga of both batches are successively brought into the analytic apparatus.

As seen from the foregoing description, the inner diameter of both tubular liquid sample batch receptacle 82 and outlet tube 84 thereof should be sufficiently small to prevent an interface between the respective liquid and nitrogen gas batches La, Ga from being destroyed. Said inner diameter varies with an interfacial tension between the liquid sample and gas used. While the inner diameter of the inlet tube 83 is not subject to any particular limitation, said inlet tube 83, liquid ample batch receptacle and outlet tube 84 should preferably have an equal inner diameter in consideration of the ease of fabrication. In FIG. 7, the inlet tube 83, liquid sample batch receptacle 82 and outlet tube 84 jointly constitute U-shaped tubing having a uniform inner diameter.

The quantities of liquid batches and gas batches formed can be freely defined by the capacity of the liquid sample receptacle 82 and the flow rates of the liquid and gas brought into said receptacle.

For illustration, there will now be described the case where there are formed alternate series of liquid and gas batches using a liquid and gas batch generator 81 having a uniform inner diameter. Now let it be assumed that the liquid sample batch receptacle 82 has a capacity of M ml, the liquid sample runs at a flow rate of N ml/min and the gas is carried at a flow rate of R ml/min. Then the liquid sample batch naturally has a quantity of M ml and the gas batch has a quantity of $(M/N) \times R$ ml.

The gas supplier 88 of FIG. 7 sends forth compressed gas to the inlet tube 83. However, said gas supplier 88 is not the only means for providing a stream of gas through the liquid sample batch receptacle 82 in a prescribed flow rate. This operation can also be effected by providing suction means on the side of the outlet tube 84.

Figure 8:
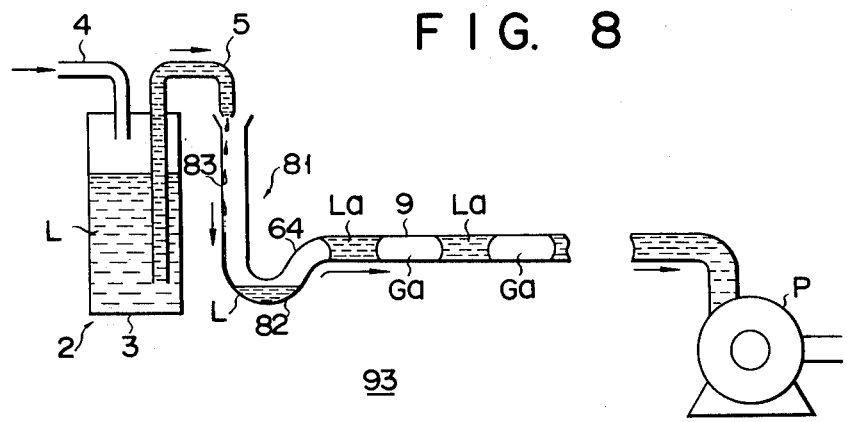
FIG. 8 is a schematic side view of a further embodiment of the batch flow-generating device used with the analytic apparatus of the invention.

A batch flow-generating device 93 shown in FIG. 8 comprises a liquid and gas batch generator 81, liquid sample supplier 2 both similar to those of FIG. 1, and suction means, for example, a suction pump P disposed downstream of the liquid and gas batch generator, for example, on the terminal tube 50 of FIG. 1. Referring to FIG. 8, the parts of the batch flow-generating device 93 the same as those of FIGS. 1 and 7 are denoted by the same numerals. The inlet port of the tube 83 of the liquid and gas flow generator 81 is open to the atmosphere. The liquid sample L held in the liquid sample storage tank 3 is delivered to the liquid and gas batch generator 81 through the connection tube 5 by the pressure of the compressed air introduced into the storage tank 3 through the gas tube 4. On the other hand, the open air is sucked into the liquid and gas batch generator 81 through the open inlet port of the tube 83 at a specified flow rate by operating the suction pump P. Obviously, supply of the liquid sample from the storage tank 3 to the liquid and gas batch generator 81 is effected so as not to fill up the inlet tube 83. With the batch flow-generating device 93 of FIG. 8, the manner in which batches of liquid sample and gas are produced in substantially the same as in the similar device 80 of FIG. 7, excepting that the liquid sample batch fully collected in the liquid sample batch receptacle 82 is sucked into the succeeding process through the outlet tube 84 by operation of the suction pump P.

The batch flow-generating device 93 of FIG. 8 enables alternate series of batches of liquid sample and gas respectively having a prescribed quantity to be more easily produced.

As seen from the foregoing description, any part of the analytic apparatus of this invention is not subject to an external force, enabling the apparatus itself to be formed of any kind of material. If constructed of glass, the apparatus can be used semipermanently. The subject apparatus has further advantages that it has a simple arrangement, and batches of liquid sample and gas can be produced easily and always in specified quantities, no matter how long the apparatus is operated continuously.

What we claim is:

1. An automatic analytic apparatus of liquids comprising:
   A. an analyzer for analyzing a liquid sample and having an inlet and an outlet for a liquid sample;
   B. fluid guide means for guiding a liquid sample therethrough to said analyzer, said quide means including a tubular conduit having an inlet and an outlet connected to the inlet of said analyzer; and
   C. a batch flow-generating device for forming a flowing series of alternate liquid and gas batches each having a prescribed volume comprising:
      a. tubular siphoning means for collecting liquid samples in a prescribed volume and then intermittently discharging them as integral liquid batches by siphon action, said siphoning means having an inlet and an outlet,
      b. supply means for supplying sample liquid into said siphoning means through its inlet at a prescribed rate so that its inlet is prevented from being closed up by sample liquid,
      c. tubular means including a peripheral side wall, an outlet and an inlet connected to the outlet of said siphoning means,
      d. receptacle means for collecting liquid samples of prescribed volume, said receptacle means having an inlet connected to the outlet of said tubular means and an outlet connected to the inlet of said fluid guide means, and
      e. branch tube means comprising a tube with first and second ends, the first end being connected to said peripheral side wall for fluid flow between said branch tube and said tubular means and said second end being open to a gas source whereby gas in prescribed volume may enter and occupy space within said tubular means between said first end connection and said tubular means inlet, whereby gas of prescribed volume is interposed between liquid batches discharged by said tubular siphoning means thus causing a flowing series of alternate liquid and gas batches from said receptacle means to pass into the inlet of said fluid means.

2. The apparatus of claim 1 wherein said fluid guide means includes adjacent the inlet of said analyzer a vertical exhaust tube having a lower end and an upper open end, the lower end of the exhaust tube being connected to the said fluid guide means for fluid flow between said exhaust tube and said guide means for fluid flow between said exhaust tube and said guide means permitting gas batches flowing in said fluid guide means to discharge through said exhaust tube and out its upper open end so that liquid batches flowing in said fluid guide means converge into an internal body to enter said analyzer.

3. The apparatus of claim 1 wherein said tubular conduit of sid fluid guide means has an inner diameter sufficiently small to maintain an interface between adjacent liquid and gas batches.

4. The apparatus of claim 3 wherein said tubular means (c) has an inner diameter sufficiently small to maintain an interface between liquid and gas batches present therein.

5. The apparatus of claim 4 wherein said batch flow-generating device includes a second branch tube means connected to said peripheral side wall of said tubular means between said inlet of said tubular means and said first end connection.

6. The apparatus of claim 4 wherein said tubular siphoning means and said receptacle means both consist of U-shaped tubes having the same capacity.

7. The apparatus of claim 1 wherein said analyzer is a colorimeter.

8. The apparatus of claim 7 which comprises color reagent addition means comprising a tube having an inlet and an outlet connected to said fluid guide means for liquid flow from said addition means into said fluid guide means and a vessel connected to the inlet of said addition means tube filled with a reagent for coloring sample liquid flowing in said fluid guide means.

9. The apparatus of claim 8 wherein said addition means tube is a U-shaped tube, the outlet of which is connected to the underside of the peripheral side wall of said fluid guide means.

10. The apparatus of claim 8 wherein said fluid guide means includes a zizzag-shaped section disposed downstream of the connection with said addition means tube so as to cause color reagent to be mixed with sample liquid flowing in said fluid guide means.

* * * * *